United States Patent [19]

Göbel et al.

[11] Patent Number: 5,663,395

[45] Date of Patent: Sep. 2, 1997

[54] PROCESS FOR THE SELECTIVE SYNTHESIS OF SILYLALKYLDISULPHIDES

[75] Inventors: Thomas Göbel; Jörg Münzenberg, both of Hanau, Germany

[73] Assignee: Degussa Aktiengesellschaft, Frankfurt, Germany

[21] Appl. No.: 743,842

[22] Filed: Nov. 5, 1996

[30] Foreign Application Priority Data

Nov. 7, 1995 [DE] Germany .................. 195 41 404.7

[51] Int. Cl.⁶ .................................................. C07F 7/08
[52] U.S. Cl. ............................................. 556/427
[58] Field of Search ................................. 556/427

[56] References Cited

U.S. PATENT DOCUMENTS

| 3,284,466 | 11/1966 | Rosenthal | 556/427 |
| 4,595,740 | 6/1986 | Panster | 556/427 X |
| 5,440,064 | 8/1995 | Agostini et al. | 556/427 |

*Primary Examiner*—Paul F. Shaver
*Attorney, Agent, or Firm*—Beveridge, DeGrandi, Weilacher & Young, L.L.P.

[57] ABSTRACT

A process is disclosed for the selective synthesis of silylalkyldisulphides by desulphurization of the corresponding polysulphides using nucleophilic reagents.

13 Claims, No Drawings

PROCESS FOR THE SELECTIVE SYNTHESIS OF SILYLALKYLDISULPHIDES

INTRODUCTION AND BACKGROUND

The present invention relates to a process for the selective synthesis of silylalkyldisulphides by the desulphurization of corresponding polysulphides with nucleophilic reagents.

Trialkoxypropylpolysulphides are excellent phase mediators for the incorporation of oxide materials into rubber matrices. In particular in the tire industry, triethoxysilylpropyltetrasulphane ($[(CH_3CH_2O)_3SiCH_2CH_2CH_2]_2S_4$) is widely used in silica-reinforced tires. In such applications, the silane, on the one hand, becomes attached to free hydroxyl groups of the silica and, on the other, undergoes vulcanization-like crosslinking with the rubber. In specific applications, it is convenient to provide the silane not with a tetrasulphane functional group, but instead with a less reactive disulphane functional group. The synthesis of silylalkyldisulphanes together with the corresponding polysulphides is described in various patents and publications.

German Patents 2 405758 and 2 542534 relate to production starting from mercaptoalkylsilanes and sulphur, in which hydrogen sulphide is released.

Various production processes start from disulphides produced in situ, with which nucleophilic substitutions are then performed on haloalkylsilanes. These processes differ only in the synthesis of the disulphide nucleophile. According to German Patent 3 311340, the disulphide is produced by reactions between hydrogen sulphide, sodium and sulphur in ethanol.

According to U.S. Pat. No. 5,405,985, preparation is performed using an aqueous sodium sulphide solution together with sulphur. It is sufficiently well know to those skilled in the art that mixtures of various polysulphides are produced in reactions between sulphides and sulphur, such that when nucleophilic substitution is performed it is only possible to produce a mixture of polysulphanes of various chain lengths. The same applies to reactions between mercaptans or thiolates and sulphur. It is moreover known that the corresponding disulphanes may be isolated from these product mixtures only with great difficulty.

While German Patent 2 360470 does indeed describe a method for the production of pure bis(silylalkyl)disulphane by oxidizing the corresponding mercaptan with sulphuryl chloride, this method results in the formation of highly corrosive secondary products ($SO_2$, HCl). Secondary reactions on the silyl residue moreover result in a reduction in the yield of the desired product (for example: 63.3%). Another oxidative variant is described in EP-A1 217178. In this variant, the corresponding thiolates are oxidized with iodine to yield the disulphides. After the elaborate production of the silylalkylmercaptan, this process requires two further reaction stages.

It is therefore an object of the present invention to obtain elevated yields of the desired silylalkyldisulphides.

SUMMARY OF THE INVENTION

The above and other objects of the present invention are achievable by a process for the production of bis(silylalkyl) disulphanes wherein silylalkylpolysulphides are reacted with a selected nucleophilic compound.

More specifically in accordance with the present invention bis(silylalkyl)disulphanes are produced having the formula:

$$(R^1R^2R^3SiR^4)_2S_2 \qquad (I),$$

in which, $R^1$, $R^2$, $R^3$: are identical or different branched or unbranched alkyl and/or alkoxy groups having a chain length of 1 to 8 C atoms, wherein at least one alkoxy group is preferably present, hydrogen or monovalent aryl residues, in particular phenyl, tolyl, benzyl;

$R^4$: is a divalent alkylidene residue having a chain length of 1 to 8 C atoms, preferably of 2 to 4 C atoms or

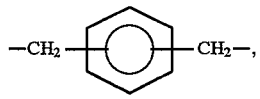

by reacting silylalkylpolysulphides (—sulphanes) or silylalkylpolysulphide mixtures of the formula:

$$(R^1R^2R^3R^4)_2S_N \qquad (II),$$

in which $R^1$, $R^2$, $R^3$ and $R^4$ have the same meaning as in formula (I), and n is an integer between 3 and 20, in particular between 3 and 10, with a nucleophilic compound of the formulae $$M^+CN^- \qquad (III) \text{ or}$$

$$M^+{}_2SO_3{}^{2-} \qquad (IV),$$

in which $M^+$ is an alkali metal cation, an ammonium ion partially or entirely substituted with $C_1$–$C_4$ alkyl or an unsubstituted ammonium ion or half an alkaline earth metal ion or zinc ion, or a nucleophilic compound of the formula $$R^5R^6R^7P \qquad (V),$$

in which $R^5$, $R^6$, $R^7$ have the same meaning as $R^1$, $R^2$, $R^3$ in the formula (I).

In carrying out this process the nucleophilic compounds of the formulae (III) to (V) are used, preferably individually but also as a mixture, in an equimolar quantity relative to the sulphur atoms to be removed from the compound according to the formula (II). The resultant solid is filtered out and the disulphane obtained is purified.

DETAILED DESCRIPTION OF THE INVENTION

The process of the invention can be performed both in a solvent-free systems and with the addition of solvent. Preferred solvents are those in which the nucleophilic compound used is at least partially soluble. The selected solvents are inert under the reaction conditions utilized.

Aliphatic solvents, such as for example alkanes such as pentane, hexane or mixtures of various branched and unbranched alkanes or aromatic solvents, such as for example benzene, toluene or xylene, or aliphatic or aromatic ethers, such as for example diethyl ether, dibenzyl ether, methyl tert.-butyl ether may be used.

The organic solvent preferably used is a linear or branched alcohol having 1–8 C atoms, such as for example methyl, ethyl, propyl, butyl or pentyl alcohol. Cycloalkyl alcohols having 5–8 C atoms, phenol or benzyl alcohol are also suitable.

In order to avoid transesterification, for example, it is convenient to use the alcohol corresponding to the group $R^1$, $R^2$, $R^3$ (alkoxy). It may optionally also be advantageous to use a mixture of these alcohols, for example if $R^1$, $R^2$, $R^3$ have different meanings in a single compound.

In a particular embodiment of the invention, the reaction is performed in a two-phase system, if the solvent, such as for example water, is not miscible with sulphane used.

In this case, a known phase transfer catalyst, for example Aliquat 336 ($C_8H_{17}$)$_3N^+CH_3CL^-$ is used in the conventional quantity (see E. V. Dehmlow, S. S. Dehmlow, *Phase Transfer Catalysis*, 2nd edition, Weinheim 1983).

The reaction may be performed both at room temperature and at higher temperatures. In order to keep reaction times as short as possible, it is convenient to perform the reaction at elevated temperatures, preferably at the boiling temperature of the solvent used.

It is immaterial to the success of the process whether it is performed without pressure or under pressure.

Performance of the invention is illustrated by the following examples.

In an advantageous embodiment of the invention, the disulphides are produced in a simplified process.

Separate production of the polysulphanes to be desulphurized has proved to be unnecessary. It is possible according to the invention to synthesize them in situ and to convert them directly into the desired disulphides in a "single vessel" process.

To this end, a solution, optionally a suspension, is prepared which contains:

a) a polysulphide or a polysulphide mixture of the formula $M^+_2S_n$, wherein $M^+$ and n have the above-stated meanings, b) a nucleophilic reagent or a mixture of different nucleophilic reagents of the formulae $M^+CN^-$, $M^+_2SO_3^{2-}$, $R^5$, $R^6$, $R^7P$, in which $M^+$, $R^5$, $R^6$, and $R^7$ have the meanings already mentioned, c) an organosilicon compound of the general formula

$$Cl—R^4—Si(R^1R^2R^3)_3 \qquad (VI),$$

in which $R^1$, $R^2$, $R^3$, and $R^4$ have the above-stated meaning, in particular in a molar ratio of 0.4 to 0.7 of (a):1 to 1.1 of (b):1 of (c).

The ratio of (a):(b) is calculated here from the number of sulphur atoms to be removed from (II).

The solvent used, in particular with regard to (VI), is preferably the alcohol which corresponds to $R^1$, $R^2$, $R^3$, from (I) in its meaning as an alkoxy group.

The sequence in which the constituents are stirred into the solvent, preferably at a temperature of 20° C. to 35° C., is of no particular significance.

The reaction proceeds at a temperature higher than the above, in particular in the range from 40° C. up to the reflux temperature of the solvent used in the mixture.

In general, a 10 to 90 wt. % solution of the organosilicon compound is used relative to the total weight of the reaction mixture.

After the reaction, the mixture is cooled, the solvent removed under a vacuum and the remaining solid purified with suitable organic solvents, in particular petroleum ether, in which the desired disulphide dissolves.

Once the solvent has been removed, the pure disulphane is obtained.

The Examples illustrate details of the procedure of this invention.

EXAMPLE 1

Desulphurization of bis(triethoxysilylpropyl) tetrasulphane with NaCN in ethanol 67.37 g (0.125 mol) of bis(triethoxysilylpropyl) tetrasulphane in 60 ml of ethanol are introduced into a 250 ml three-necked flask equipped with a magnetic stirrer and reflux condenser. 12.25 g (0.250 mol) of pulverulent sodium cyanide are added to this mixture. The mixture is refluxed for 4 hours. After cooling to room temperature, the solvent is distilled off in a rotary evaporator. The solid/liquid mixture is allowed to stand for 2 hours at room temperature until the solid has completely crystallized and the mixture is filtered. The filter cake is washed three times with 50 ml of petroleum ether. Once the petroleum ether has been stripped out of the filtrate, pure bis(triethoxysilylpropyl)disulphane is obtained (verified by $^1$H-NMR spectroscopy).

Yield: 97%.

EXAMPLE 2

Desulphurization of bis(triethoxysilylpropyl) tetrasulphane with KCN in ethanol 67.34 kg (125 mol) of bis(triethoxysilylpropyl) tetrasulphane in 60 l of ethanol are introduced into a 200 l glass distillation boiler equipped with a high speed stirrer. 16.28 kg (250 mol) of solid potassium cyanide is then stirred in. The mixture is refluxed for 4 hours under nitrogen. Once the solvent has been stripped out at 80° C. under a vacuum, the mixture is allowed to cool and the precipitated solid filtered out. The filter residue is washed three times with 10 l portions of petroleum ether. The solvent is removed from the filtrate at 70° C. under a vacuum. 58.8 kg (124 mol) of pure bis(triethoxysilyl-propyl)disulphane are obtained (verified by $^1$H-NMR spectroscopy).

Yield: 99%

EXAMPLE 3

Desulphurization of bis(triethoxysilylpropyl) tetrasulphane with NaCN in a two-phase system 19.6 g (0.4 mol) of NaCN in 160 ml of water are introduced into a 500 ml three-necked flask equipment with a magnetic stirrer, reflux condenser and dropping funnel and heated to 90° C. Once this temperature has been reached, a mixture of 107.8 g (0.2 mol) of bis(triethoxysilylpropyl) tetrasulphane, 120 ml of toluene and 5 g of phase transfer catalyst Aliquat 336 is added dropwise within 45 minutes. Once addition is complete, the mixture is stirred for a further 2 hours at this temperature, cooled and 12.4 g of insoluble material is finally filtered out. The organic and aqueous phases of the filtrate are separated and the organic phase evaporated under a vacuum. 90.4 g (0.19 mol) of pure bis(triethoxysilylpropyl)disulphane are obtained (verified by $^1$H-NMR spectroscopy).

Yield: 95%.

EXAMPLE 4

Desulphurization of bis (triethoxysilylpropyl) tetrasulphane with triphenylphosphane in ethanol 67.37 g (0.125 mol) of bis(triethoxysilylpropyl) tetrasulphane in 60 ml of ethanol are introduced into a 250 ml three-necked flask equipped with a magnetic stirrer and reflux condenser. 65.57 g (0.250 mol) of solid triphenylphosphane are added to this mixture. The mixture is refluxed for 4 hours. After cooling to room temperature, the solvent is distilled off in a rotary evaporator. The solid/liquid mixture is allowed to stand for 2 hours at room temperature until the solid has completely crystallized and the mixture is filtered. The filter cake is washed three times with 50 ml of petroleum ether. Once the petroleum ether has been stripped out of the filtrate, pure bis(triethoxysilylpropyl)disulphane is obtained (verified by ¹H-NMR spectroscopy).

Yield: 98%.

EXAMPLE 5

Desulphurization of bis(triethoxysilylpropyl) tetrasulphane, with sodium sulphite hydrate A mixture of 160 ml of water and 105.9 g (0.85 mol) of sodium sulphite hydrate is heated to 90° C. in a 1000 ml three-necked flask equipped with a KPG stirrer, reflux condenser and dropping funnel. A mixture of 226.4 g (0.42 mol) of bis(triethoxysilyl-propyl)tetrasulphane, 20 ml of ethanol and 5.0 g of Aliquat 336 are added dropwise within 30 minutes at this temperature. Once addition is complete, a further 100 ml of ethanol are added and the mixture stirred for 3.5 hours at 80° C. Once the reaction mixture has cooled to room temperature, the aqueous phase is separated. The solvent is removed from the organic phase by vacuum distillation in a rotary evaporator. 198.9 g (0.41 mol) of bis(triethoxysilylpropyl)disulphane are obtained (verified by ¹H-NMR spectroscopy).

Yield: 99%

EXAMPLE 6

Desulphurization of bis(triethoxysilylpropyl) tetrasulphane produced in situ with NaCN A mixture of 43.5 g (0.25 mol) of a polysulphide of the average composition $Na_2S_4$, 24.5 g (0.5 mol) of NaCN and 120.4 g (0.5 mol) of chloropropyltriethoxysilane in 120 ml of ethanol are introduced into a 500 ml three-necked flask equipped with a magnetic stirrer and reflux condenser and refluxed for 2 hours. Once the product mixture has cooled to room temperature, the solvent is removed under a vacuum, the remaining residue is redissolved with 150 ml of petroleum ether and filtered. The filter residue is washed three times with 50 ml portions of petroleum ether. The solvent is removed from the combined filtrates under a vacuum. 108.7 g (0.21 mol) of the pure disulphane are obtained (verified by ¹H-NMR spectroscopy).

Yield: 94%

Further variations and modifications will become apparent to those skilled in the art from the foregoing and are intended to be encompassed by the claims appended hereto.

German priority application 195 41 404.7 is relied on and incorporated herein by reference.

We claim:
1. A process for the production of bis(silylalkyl)-disulphanes of the formula:

$$(R^1R^2R^3SiR^4)_2S_2 \qquad (I),$$

in which, $R^1$, $R^2$, $R^3$: are identical or different branched or unbranched alkyl and/or alkoxy groups having a chain length of 1 to 8 C atoms, hydrogen or monovalent aryl, $R^4$: is a divalent alkylidene residue having a chain length of 1 to 8 C atoms,

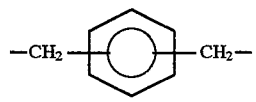

comprising reacting a silylalkylpolysulphide or mixture of silylalkylpolysulphide of the formula:

$$(R^1R^2R^3SiR^4)_2S_n \qquad (II),$$

in which $R^1$, $R^2$, $R^3$ and $R^4$ have the same meaning as in formula (I), and n is an integer from 3 to 20, with a nucleophilic compound of the formulae:

$$M^+CN^- \qquad (III) \text{ or}$$

$$M^+{}_2SO_3{}^{2-} \qquad (IV),$$

in which $M^+$ is an alkali metal cation, a substituted or unsubstituted ammonium ion or half an alkaline earth metal ion or zinc ion, or of the formula $$R^5R^6R^7P \qquad (V),$$

in which $R^5$, $R^6$, $R^7$ have the same meaning as $R^1$, $R^2$, $R^3$ in the formula (I), wherein the compounds of the formulae (III) to (V) are in an equimolar quantity relative to the sulphur atoms to be removed from the compound according to the formula (II).

2. The process according to claim 1, wherein $R^4$ is a divalent alkylidene residue of 2 to 4 C atoms.

3. The process according to claim 1, wherein the compounds of the formulae (III) to (V) are used as a mixture.

4. The process according to claim 1, further comprising reacting in the presence of a solvent which dissolves the nucleophilic compound.

5. The process according to claim 1, further comprising reacting at a temperature of between 20° C. and the boiling temperature of the solvent used.

6. The process according to claim 1, further comprising reacting in a two-phase system in the presence of a phase transfer catalyst.

7. The process according to claim 1, further comprising filtering the resultant solid.

8. The process according to claim 1, wherein the silylakylpolysulphane of the formula (II) which is reacted is synthesized in situ by producing a solution which contains a) a polysulphide or a polysulphide mixture of the formula $M^+{}_2S_n$, wherein $M^+$ and n have the same meaning as in formula III, b) a nucleophilic reagent from the group consisting of $M^+CN^-$, $M^+{}_2SO_3{}^{2-}$, $R^5R^6R^7P$, and mixtures thereof wherein: $M^+$, $R^5$, $R^6$, $R^7$ have the meaning in formula III, IV and V c) an organosilicon compound of the formula $$Cl\text{-}R^4\text{-}Si\ (R^1R^2R^3)\ [^3]_3 \qquad (VI),$$

in which $R^1$, $R^2$, $R^3$ and $R^4$ have the meaning in formula I in a molar ratio of 0.4 to 0.7 of (a) : 1 to 1.1 of (b) : 1 of (c), and reacting to form the desired disulphide.

9. The process according to claim 8 further comprising separating the resultant solid from said solution.

10. The process according to claim 3, further comprising reacting in the presence of a solvent which dissolves the nucleophilic compound.

11. The process according to claim 3, further comprising reacting at a temperature of between 20° C. and the boiling temperature of the solvent used.

12. The process according to claim 3 further comprising reacting in a two-phase system in the presence of a phase transfer catalyst.

13. A process for the production of bis(silylalkyl)-disulphanes of the formula:

$$(R^1R^2R^3SiR^4)_2S_2 \quad (I),$$

in which, $R^1$, $R^2$, $R^3$: are identical or different branched or unbranched alkyl and/or alkoxy groups having a chain length of 1 to 8 C atoms, hydrogen or monovalent aryl, $R^4$: is a divalent alkylidene residue having a chain length of 1 to 8 C atoms, or

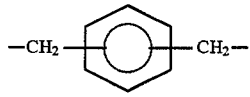

comprising reacting a silylalkylpolysulphide or mixture of silylalkylpolysulphide of the formula:

$$(R^1R^2R^3SiR^4)_2S_n \quad (II),$$

in which $R^1$, $R^2$, $R^3$ and $R^4$ have the same meaning as in formula (I), and n is an integer from 3 to 20, with a nucleophilic compound of the formulae:

$$M^+CN^- \quad (III) \text{ or}$$

$$M^+_2SO_3^{2-} \quad (IV),$$

in which $M^+$ is an alkali metal cation, a substituted or unsubstituted ammonium ion or half an alkaline earth metal ion or zinc ion, or of the formula $$R^5R^6R^7 \quad (V),$$

in which $R^5$, $R^6$, $R^7$ have the same meaning as $R^1$, $R^2$, $R^3$ in the formula (I), wherein the compounds of the formulae (III) to (V) are in an equimolar quantity relative to the sulphur atoms to be removed from the compound according to the formula (II), said reaction being performed in a two-phase system in the presence of a phase transfer catalyst and thereafter recovering the desired compound.

* * * * *

UNITED STATES PATENT AND TRADEMARK OFFICE
CERTIFICATE OF CORRECTION

PATENT NO. : 5,663,395
DATED : September 2, 1997
INVENTOR(S) : Thomas Goebel, et al.

It is certified that error appears in the above-identified patent and that said Letters Patent is hereby corrected as shown below:

Column 2, line 18, change "$(R^1R^2R^3R^4)_2S_N$" to --$(R^1R^2R^3R^4)_2S_n$--
line 49 delete "a".

Column 3, line 8, change "$(C_8H_{17})_3N^+CH_3CL^-$" to --$(C_8H_{17})_3N^+CH_3Cl^-$--.

lines 33-34, change "$R^5, R^6, R^7P$" to --$R^5R^6R^7P$--;

Column 6, line 56, change "$Cl-R^4-Si(R^1R^2R^3)[^3]_3$" to --$Cl-R^4-Si(R^1R^2R^3)_3$--.

Column 7, line 6, change "_$(R^1R^2R^3SiR^4)_2S_2$" to --$(R^1R^2R^3SiR^4)_2S_2$--.

Column 8, line 11, change "$R^5R^6R^7$" to --$R^5R^6R^7P$--.

Signed and Sealed this

Seventeenth Day of February, 1998

Attest:

BRUCE LEHMAN

Attesting Officer      Commissioner of Patents and Trademarks